US012318466B2

(12) United States Patent
Bruen, Jr. et al.

(10) Patent No.: US 12,318,466 B2
(45) Date of Patent: Jun. 3, 2025

(54) HAIR CLEANSER

(71) Applicant: AJINOMOTO CO., INC., Tokyo (JP)

(72) Inventors: Richard J. Bruen, Jr., Itasca, IL (US); Naoaki Ikeda, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 836 days.

(21) Appl. No.: 17/199,899

(22) Filed: Mar. 12, 2021

(65) Prior Publication Data
US 2021/0267869 A1 Sep. 2, 2021

Related U.S. Application Data

(63) Continuation of application No. PCT/JP2019/036270, filed on Sep. 17, 2019.

(60) Provisional application No. 62/732,738, filed on Sep. 18, 2018.

(51) Int. Cl.
| | | |
|---|---|---|
| *A61K 8/46* | (2006.01) | |
| *A61K 8/20* | (2006.01) | |
| *A61K 8/41* | (2006.01) | |
| *A61K 8/44* | (2006.01) | |
| *A61K 8/73* | (2006.01) | |
| *A61Q 5/02* | (2006.01) | |
| *A61Q 5/12* | (2006.01) | |

(52) U.S. Cl.
CPC .......... *A61K 8/466* (2013.01); *A61K 8/20* (2013.01); *A61K 8/416* (2013.01); *A61K 8/44* (2013.01); *A61K 8/731* (2013.01); *A61Q 5/02* (2013.01); *A61Q 5/12* (2013.01); *A61K 2800/5426* (2013.01)

(58) Field of Classification Search
None
See application file for complete search history.

(56) References Cited

U.S. PATENT DOCUMENTS

| | | |
|---|---|---|
| 2013/0216491 A1 | 8/2013 | Ogihara et al. |
| 2014/0079658 A1 | 3/2014 | Terazaki et al. |
| 2014/0112879 A1 | 4/2014 | Molenda et al. |
| 2015/0275133 A1 | 10/2015 | Doi |
| 2017/0281497 A1 | 10/2017 | Kobayashi |

FOREIGN PATENT DOCUMENTS

| | | | | |
|---|---|---|---|---|
| EP | 1746141 A1 | * | 1/2007 | ............... A61K 8/44 |
| JP | 2004-161758 A | | 6/2004 | |
| JP | 2006-282565 A | | 10/2006 | |
| JP | 4979126 B2 | | 7/2012 | |
| JP | 2015-27977 A | | 2/2015 | |
| JP | 2016041729 A | * | 3/2016 | |
| JP | 2016-210775 A | | 12/2016 | |
| JP | 2017081905 A | * | 5/2017 | |
| JP | 6180202 B2 | | 8/2017 | |
| WO | WO 2016/104692 A1 | | 6/2016 | |
| WO | WO-2017179627 A1 | * | 10/2017 | ............... A61K 8/37 |

OTHER PUBLICATIONS

Office Action issued Oct. 10, 2023, in corresponding Japanese Patent Application No. 2020-548488 (English Translation only), 3 pages.
Udo Walz, Germany, Detox Shampoo, Mintel GNPD, 2016, ID#4379609, Internet URL:https://portal.mintel.com , 3 pages.
Japanese Office Action issued May 23, 2023 in Japanese Patent Application No. 2020-548488 (submitting unedited computer-generated English translation only), 4 pages.

* cited by examiner

*Primary Examiner* — Nannette Holloman
(74) *Attorney, Agent, or Firm* — Oblon, McClelland, Maier & Neustadt, L.L.P.

(57) ABSTRACT

Hair cleansing agents containing the following components (A) to (E) and water:
(A) not less than 3 wt % and not more than 12 wt % of one or more kinds selected from the group consisting of acyl isethionate and α-olefin sulfonate
(B) not less than 0.5 wt % and not more than 10 wt % of acyl acidic amino acid or a salt thereof,
(C) not less than 0.005 wt % and not more than 0.8 wt % of a cationic polymer,
(D) not less than 0.25 wt % and not more than 3 wt % of one or more kinds selected from the group consisting of dibasic acid, PCA and salts thereof, and
(E) an inorganic salt,
are superior in foaming performance, imparting conditioning property in a series of hair washing processes of washing, rinsing and drying, and hair appearance after drying.

9 Claims, No Drawings

HAIR CLEANSER

CROSS REFERENCES TO RELATED APPLICATIONS

This application is a continuation of International Patent Application No. PCT/JP2019/036270, filed on Sep. 17, 2019, and claims priority to U.S. Provisional Patent Application No. 62/732,738, filed on Sep. 18, 2018, both of which are incorporated herein by reference in their entireties.

BACKGROUND OF THE INVENTION

Field of the Invention

The present invention relates to hair cleansing agents which are superior in lather properties and texture during washing hair.

Discussion of the Background

Hair is always affected by ultraviolet rays from sunlight, dryness and the like, and tends to become dry and lose its luster due to brushing, heat from a dryer, and the like in daily hair care. In recent years, since hair coloring and perming have become popular, hair often suffers from chemical damage, and problems occur such as damage of hair surface, increased friction between hairs, less smooth passage of finger through hair, and reduced gloss of hair.

To deal with such problems, hair cleansing agents have been proposed such as an aqueous hair cleansing agent composed of a combination of an anionic surfactant having a sulfuric acid residue, an alcohol having a cyclic structure, and an organic carboxylic acid (see JP Patent 6180202, which is incorporated herein by reference in its entirety), a hair cleansing agent composed of a combination of a plant extract, lactic acid or citric acid or glutamic acid, and a vegetable oil (see JP Patent 4979126, which is incorporated herein by reference in its entirety), a scalp hair cleansing composition composed of a combination of an acylamino acid-based surfactant, an amphoteric surfactant, a nonionic surfactant, and a cationic polymer (see JP-A-2016-210775, which is incorporated herein by reference in its entirety), a shampoo composition composed of a combination of an anionic surfactant, an amphoteric surfactant, a cationic polymer, and a hair repair component (see JP-A-2006-282565, which is incorporated herein by reference in its entirety), and the like. However, it is difficult to simultaneously achieve, in addition to foaming performance, smooth passage of finger through hair during washing, smooth passage of finger through hair during rinsing, smooth passage of finger through hair after drying, and improvement of gloss.

In recent years, moreover, with the spread of the laureth sulfate-free concept, the number of cases where α-olefin sulfonate is used as a main surfactant is increasing. However, the conditioning effect as a hair cleansing agent is not satisfactory. When the laureth sulfate-free concept is insisted, silicon-free is often requested at the same time. However, it is difficult to exert a conditioning effect without blending a silicone compound.

SUMMARY OF THE INVENTION

Accordingly, it is one object of the present invention aims to provide silicon-free hair cleansing agents capable of imparting a conditioning effect in a series of hair washing processes of washing, rinsing and drying, and an excellent hair appearance after drying, in addition to good foaming performance.

This and other objects, which will become apparent during the following detailed description, have been achieved by the inventors' discovery that a composition containing acyl isethionate or α-olefin sulfonate, acyl acidic amino acid or a salt thereof, cationic polymer, dibasic acid or PCA, and inorganic salts at a specific mixing ratio affords a composition superior in foaming performance, and the like, smooth passage of finger through hair during hair washing processes, appearance such as shiny hair after drying and the like, and texture of hair such as moist feeling and the like.

Accordingly, the present invention provides the following.

(1) A hair cleansing agent comprising the following components (A) to (E) and water:
   (A) not less than 3 wt % and not more than 12 wt % of one or more kinds selected from the group consisting of acyl isethionate and α-olefin sulfonate
   (B) not less than 0.5 wt % and not more than 10 wt % of acyl acidic amino acid or a salt thereof,
   (C) not less than 0.005 wt % and not more than 0.8 wt % of a cationic polymer,
   (D) not less than 0.25 wt % and not more than 3 wt % of one or more kinds selected from the group consisting of dibasic acid, PCA and salts thereof, and
   (E) an inorganic salt.

(2) The hair cleansing agent of (1), further comprising component (F) not less than 0.01 wt % and not more than 2 wt % of a basic or neutral amino acid.

(3) The hair cleansing agent of (1) or (2), wherein the component (B) acyl acidic amino acid is acylglutamic acid.

(4) The hair cleansing agent of (3), wherein the component (B) acylglutamic acid has an acyl chain length of C8 to C20.

(5) The hair cleansing agent of any of (1) to (4), wherein the component (C) cationic polymer has a nitrogen content of not less than 1.5 wt % and not more than 2.2 wt %.

(6) The hair cleansing agent of any of (1) to (5), wherein the component (D) dibasic acid is glutamic acid.

(7) The hair cleansing agent of any of (1) to (6), wherein the (E) inorganic salt is sodium chloride, potassium chloride or magnesium chloride.

(8) The hair cleansing agent of any of (1) to (7), wherein the agent is in a liquid form.

(9) The hair cleansing agent of (8), wherein the agent has a pH of less than 7.

(10) A method for washing hair or scalp, comprising a step of applying a hair cleansing agent comprising the following components (A) to (E) and water:
   (A) not less than 3 wt % and not more than 12 wt % of one or more kinds selected from the group consisting of acyl isethionate and α-olefin sulfonate
   (B) not less than 0.5 wt % and not more than 10 wt % of acyl acidic amino acid or a salt thereof,
   (C) not less than 0.005 wt % and not more than 0.8 wt % of a cationic polymer,
   (D) not less than 0.25 wt % and not more than 3 wt % of one or more kinds selected from the group consisting of dibasic acid, PCA and salts thereof, and
   (E) an inorganic salt, to hair or scalp.

(11) Use of the following components (A) to (E) in producing a hair cleansing agent:
   (A) not less than 3 wt % and not more than 12 wt % of one or more kinds selected from the group consisting of acyl isethionate and α-olefin sulfonate (B) not less than 0.5 wt % and not more than 10 wt % of acyl acidic amino acid or a salt thereof (C) not less than 0.005 wt % and not more than 0.8 wt % of a cationic polymer (D) not less than 0.25 wt % and not more than 3 wt % of one or more kinds selected from the group consisting of dibasic acid, PCA and salts thereof, and (E) an inorganic salt.

(12) Use of the following components (A) to (E) in washing hair or scalp:

(A) not less than 3 wt % and not more than 12 wt % of one or more kinds selected from the group consisting of acyl isethionate and α-olefin sulfonate (B) not less than 0.5 wt % and not more than 10 wt % of acyl acidic amino acid or a salt thereof (C) not less than 0.005 wt % and not more than 0.8 wt % of a cationic polymer (D) not less than 0.25 wt % and not more than 3 wt % of one or more kinds selected from the group consisting of dibasic acid, PCA and salts thereof, and (E) an inorganic salt.

Effects of Invention

According to the present invention, a cleansing agent superior in usability and capable of achieving quick foaming and abundant lather amount can be provided.

According to the present invention, a cleansing agent for hair and scalp which is superior in a conditioning effect can be provided.

DETAILED DESCRIPTION OF THE PREFERRED EMBODIMENTS

The present invention relates to a hair cleansing agent containing the following components (A) to (E):

(A) not less than 3 wt % and not more than 12 wt % of one or more kinds selected from the group consisting of acyl isethionate and α-olefin sulfonate (B) not less than 0.5 wt % and not more than 10 wt % of acyl acidic amino acid or a salt thereof, (C) not less than 0.005 wt % and not more than 0.8 wt % of a cationic polymer, (D) not less than 0.25 wt % and not more than 3 wt % of one or more kinds selected from the group consisting of dibasic acid, PCA and salts thereof, and (E) an inorganic salt (hereinafter sometimes to be abbreviated as the cleansing agent of the present invention).

The component (A) in the present invention is one or more kinds selected from the group consisting of acyl isethionate and α-olefin sulfonate of, and is an anionic surfactant having sulfonate as a hydrophilic group.

The acyl group of acyl isethionate is an acyl group derived from a fatty acid having 8 to 20 carbon atoms, and an acyl group derived from a fatty acid having 8 to 18 carbon atoms is preferable, and an acyl group derived from a fatty acid having 10 to 18 carbon atoms is more preferable. That is, the acyl chain length of acyl isethionate is C8 to C20, preferably C8 to C18, more preferably C10 to C18.

Examples of the acyl group include an acyl group derived from lauric acid, myristic acid, palmitic acid, stearic acid, oleic acid, isostearic acid or the like, a mixture thereof such as beef tallow fatty acid, coconut oil fatty acid, palm kernel oil fatty acid and the like can be mentioned, an acyl group induced from lauric acid, myristic acid or coconut oil fatty acid is preferable, and an acyl group induced from lauric acid or coconut oil fatty acid is more preferable.

As a salt of acyl isethionic acid, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. Among these, alkali metal salt and alkanolamine salt are preferable, and sodium salt, potassium salt and triethanolamine salt are more preferable, from the aspect of foaming power.

As acyl isethionate, sodium cocoyl isethionate (sodium coconut oil fatty acid ethyl ester sulfonate), sodium lauric acid ethyl ester sulfonate, triethanolamine coconut oil fatty acid ethyl ester sulfonate and the like can be mentioned, and sodium cocoyl isethionate is preferable.

The α-olefin sulfonate in component (A) is alkenylsulfonate, hydroxyalkane sulfonate or a mixture thereof. The carbon atom number of α-olefin sulfonate in component (A) is 10 to 22 (olefin (C10 to 22)sulfonate), preferably 12 to 18 (olefin (C12 to 18)sulfonate), more preferably 14 to 16 (olefin (C14 to 16)sulfonate). As the α-olefin sulfonate, a mixture of two or more kinds of α-olefin sulfonates having different carbon atom numbers may be used.

As a salt of α-olefin sulfonate, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. Among these, alkali metal salt and alkanolamine salt are preferable, and sodium salt, potassium salt, and triethanolamine salt are more preferable, from the aspect of foaming power.

As α-olefin sulfonate, sodium (C14) olefin sulfonate, sodium (C14 to 16) olefin sulfonate, sodium (C14 to 18) olefin sulfonate can be mentioned, and sodium (C14 to 16) olefin sulfonate is preferable.

The content of component (A) is generally not less than 3 wt %, preferably not less than 5 wt %, more preferably not less than 7 wt %, of the whole cleansing agent, from the aspect of improvement of the lather amount. To maintain good texture after hair washing, it is generally not more than 12 wt %, preferably not more than 11 wt % is preferable, more preferably not more than 10 wt %, of the whole cleansing agent.

The component (B) in the present invention is an acyl acidic amino acid or a salt thereof.

As the acyl acidic amino acid, any of D form, L form and DL form can be used. Each of the acyl acidic amino acid or a salt thereof may be used alone, or two or more kinds thereof may be used in a mixture at any ratio.

The acyl group of acyl acidic amino acid is an acyl group derived from a fatty acid having 8 to 20 carbon atoms, and an acyl group derived from a fatty acid having 8 to 18 carbon atoms is preferable, and an acyl group derived from a fatty acid having 10 to 18 carbon atoms is more preferable. That is, the acyl chain length of the acyl acidic amino acid is C8 to C20, preferably C8 to C18, more preferably C10 to C18.

Examples of the acyl group include an acyl group derived from lauric acid, myristic acid, palmitic acid, stearic acid, oleic acid, isostearic acid or the like, a mixture thereof such as beef tallow fatty acid, coconut oil fatty acid, palm kernel oil fatty acid and the like can be mentioned, an acyl group derived from lauric acid, myristic acid or coconut oil fatty acid is preferable, and an acyl group derived from lauric acid or coconut oil fatty acid is more preferable.

While the acidic amino acid of the acyl acidic amino acid is not particularly limited as long as it is an acidic amino acid, examples thereof include glutamic acid, aspartic acid and the like, and glutamic acid is more preferable.

As a salt of acyl acidic amino acid, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. Among these, alkali metal salt and alkanolamine salt are preferable, and sodium salt, potassium salt, triethanolamine are more preferable, from the aspect of maintenance of solubility.

A salt of acyl acidic amino acid may be in the form of a salt that is obtained by adding, when the cleansing composition of the present invention is prepared, acyl acidic amino acid together with a substance (e.g., sodium hydroxide, potassium hydroxide, TEA etc.) that forms the above-mentioned salts, thus performing neutralization.

Specific examples of the acyl acidic amino acid and a salt thereof include N-lauroylglutamic acid, N-myristoylglutamic acid, N-cocoyl (coconut oil fatty acid acyl) glutamic acid, N-lauroylaspartic acid, N-myristoylaspartic acid, and N-cocoylaspartic acid, and monosodium salts thereof, monopotassium salts thereof, triethanolamine salts thereof and the like. One kind of these may be used or two or more kinds thereof may be used in a mixture. Among these, N-lauroylglutamic acid, N-myristoylglutamic acid, and N-cocoylglutamic acid, sodium salts thereof, potassium salts thereof and triethanolamine salts thereof are preferable, and N-lauroylglutamic acid and N-cocoylglutamic acid, potassium salts thereof, sodium salts thereof and triethanolamine salts thereof are more preferable.

The content of component (B) is generally not less than 0.5 wt %, preferably not less than 1 wt %, more preferably not less than 1.5 wt %, of the whole cleansing agent, from the aspect of improvement of the texture. To construct a viscosity easy to use when in use, it is generally not more than 10 wt %, preferably not more than 5 wt %, more preferably not more than 3 wt %, of the whole cleansing agent.

The component (C) in the present invention is a cationic polymer.

The weight average molecular weight of the cationic polymer is generally 10,000 to 10,000,000, preferably 100,000 to 2,000,000. Specific examples thereof include cationic cellulose, cationic starch, cationic guar gum, cationic tara gum, cationic locust bean gum, cationic fenugreek gum, diallyldialkyl quaternary ammonium salt/acrylamide copolymer, diallyldialkyl quaternary ammonium salt/acrylamide/acrylic acid copolymer and the like. Among these, cationic cellulose, and cationic guar gum are preferable since they are easily available, and cationic cellulose is preferable from the aspect of texture.

The nitrogen content of the cationic polymer is generally not less than 0.4 wt %, preferably not less than 1.2 wt %, more preferably not less than 1.5 wt %, from the aspect of texture. From the aspect of compatibility with anionic surfactants, it is generally not more than 3 wt %, preferably not more than 2.5 wt %, more preferably not more than 2.2 wt %.

The content of component (C) is generally not less than 0.005 wt %, preferably not less than 0.01 wt %, more preferably not less than 0.1 wt %, of the whole cleansing agent, from the aspect of improvement of the texture. To prevent excessive stickiness left on the hair, it is generally not more than 0.8 wt %, preferably not more than 0.5 wt %, more preferably not more than 0.3 wt %, of the whole cleansing agent.

The component (D) in the present invention is one or more kinds selected from the group consisting of a dibasic acid, pyrrolidonecarboxylic acid (PCA) and salts thereof.

The dibasic acid is not particularly limited as long as it is a dibasic acid having two carboxyl groups, and examples thereof include glutamic acid, aspartic acid, succinic acid, malonic acid, oxalic acid, maleic acid, itaconic acid, phthalic acid, adipic acid, glutar acid, tartaric acid, sebacic acid and the like. It may be an optical isomer. As the dibasic acid, glutamic acid and aspartic acid are preferable from the aspect of texture.

As salts of dibasic acid and pyrrolidonecarboxylic acid, alkali metal salts such as lithium salt, sodium salt, potassium salt and the like; alkaline earth metal salts such as calcium salt, magnesium salt and the like; alkanolamine salts such as monoethanolamine salt, diethanolamine salt, triethanolamine (TEA) salt and the like; ammonium salt; and salt of basic organic substance and the like can be mentioned. Among these, alkali metal salt and alkanol amine salt are preferable from the aspect of solubility, and sodium salt, potassium salt, and triethanolamine salt are more preferable from the aspect of texture.

In addition, a salt of dibasic acid or pyrrolidonecarboxylic acid may be in the form of a salt that is obtained by adding, when the cleansing agent of the present invention is prepared, dibasic acid or pyrrolidonecarboxylic acid together with a substance (e.g., sodium hydroxide, potassium hydroxide, TEA etc.) that forms the above-mentioned salts, thus performing neutralization.

The content of component (D) is generally not less than 0.25 wt %, preferably not less than 0.3 wt %, more preferably not less than 0.35 wt %, of the whole cleansing agent, from the aspect of improvement of the texture. To maintain solubility, it is generally not more than 3 wt %, preferably not more than 2 wt %, more preferably not more than 1 wt %, of the whole cleansing agent.

The component (E) in the present invention is an inorganic salt. While the inorganic salt is not particularly limited, an alkali metal or alkaline earth metal salts of a mineral acid, such as sulfuric acid, hydrochloric acid, phosphoric acid and the like, or carbonic acid are preferable. Specifically, sodium chloride, potassium chloride, magnesium chloride, calcium chloride, sodium sulfate, potassium sulfate, magnesium sulfate, calcium sulfate, sodium hydrogen sulfate, potassium hydrogen sulfate, monosodium phosphate, disodium phosphate, sodium carbonate, sodium hydrogen carbonate, potassium carbonate, potassium hydrogen carbonate, magnesium carbonate, calcium carbonate and the like can be mentioned. Among these, sodium chloride, potassium chloride, and magnesium chloride are preferable from the aspect of the thickening effect. Only one kind of the inorganic salt of component (E) may be used, or two or more kinds thereof may be used in combination.

The content of component (E) is generally not less than 0.01 wt %, preferably not less than 0.1 wt %, more preferably not less than 0.15 wt %, of the whole cleansing agent, from the aspect of thickening. To maintain solubility, it is generally not more than 5 wt %, preferably not more than 4 wt %, more preferably not more than 3 wt %, of the whole cleansing agent.

The content of water in the cleansing agent of the present invention is generally not less than 40 wt %, preferably not less than 50 wt %, more preferably not less than 60 wt %, further preferably not less than 70 wt %, of the whole cleansing agent. It is generally not more than 90 wt %, preferably not more than 75 wt %, more preferably not more than 60 wt %, of the whole cleansing agent.

The cleansing agent of the present invention may further contain component (F) a basic or neutral amino acid.

As the basic amino acid, arginine, lysine, and histidine can be mentioned, and arginine is preferable from the aspect of texture.

As the neutral amino acid, glycine, alanine, serine, phenylalanine, tyrosine, cysteine, and methionine can be mentioned, and glycine and alanine are preferable from the aspect of texture.

The content of component (F) is generally not less than 0.01 wt %, preferably not less than 0.03 wt %, more preferably not less than 0.05 wt %, of the whole cleansing agent, from the aspect of texture. To maintain solubility, it is generally not more than 2 wt %, preferably not more than 1 wt %, more preferably not more than 0.5 wt %, of the whole cleansing agent.

As components (A) to (F) in the present invention, synthesized products and commercially available products can be used.

The form of the cleansing agent of the present invention may be, for example, liquid, paste, gel, cream, foam or the like. Among these, liquid, paste, and cream are preferable, and liquid and cream are particularly preferable, since they are easy to fill in tubes and superior in usability.

Since the cleansing agent of the present invention shows a high conditioning effect, it can be prepared not only as hair shampoo but also scalp shampoo or rinse in shampoo.

When the cleansing agent of the present invention is a liquid, its pH is generally less than 7. It is preferably a pH of 6.8 to 4.8, more preferably a pH of 5.8 to 4.8, from the aspect of thickening. The pH can be measured by a known method.

When the cleansing agent of the present invention is other than a liquid, its pH is defined to be pH of a 1% aqueous solution thereof (25° C.), which is in accordance with the above-mentioned pH ranges.

The cleansing agent of the present invention can be produced by a method known per se. For example, a mixture of the above-mentioned respective components and other additives are mixed, and the mixture is generally heated at 65 to 85° C. to for 30 min to 1 hr to uniformly dissolve each component. The composition in a molten state can be prepared as a cleansing agent in a desired form by a method known per se. For example, a liquid cleansing agent can be obtained by the method of JP Patent 4979126, which is incorporated herein by reference in its entirety. In addition, a powder or a granular cleaning agent can be obtained by removing water from the cleansing agent of the present invention by a method known per se. Alternatively, each component is uniformly dissolved by heating, which is injected in a mold, solidified by cooling, and dried and matured to give a solid cleansing agent.

Various generally-used additives can be added to the cleansing agent of the present invention as long as the effect of the invention is not inhibited.

For example, starting materials and the like described in various official compendia such as Japanese Standards of Cosmetic Ingredients, Cosmetic Ingredients Codex, Japanese Standard of Quasi-drug Ingredients, the Japanese Pharmacopoeia, Japanese Standards for Pharmaceutical Ingredient, Japan's Specifications and Standards for Food Additives and the like, such as higher alcohols such as cetyl alcohol, stearyl alcohol, behenyl alcohol, isostearyl alcohol, octyldodecanol, oleyl alcohol, myristyl alcohol and the like; lauric acid, myristic acid, palmitic acid, stearic acid, higher fatty acids such as hardened beef tallow fatty acid, coconut oil fatty acid, palm oil fatty acid and the like and a salt thereof; moisturizers such as trimethylglycine and the like; surfactants such as anionic surfactant (excluding (A) in the present invention), cationic surfactant, amphoteric surfactant, non-ionic surfactant and the like; synthetic fats and oils such as vegetable oil, animal fats and oils, natural fat and oil derivatives, mineral fats and oils, lower and higher fatty acid ester and the like; silicone compound; polymer substance (excluding (C) in the present invention); animal and plant extracts; amino acid (excluding (D) in the present invention); nucleic acid; vitamin; enzyme; anti-inflammatory agent; antimicrobial agent; preservative; antioxidant; ultraviolet absorber; chelating agent; adiaphoretic; oxidation dye; pH adjuster; pearly sheen agent; and the like can be mentioned.

The cleansing agent of the present invention is used in the same manner as known hair cleansing agents. That is, hair is washed with water, the cleaning agent of the present invention is applied to the hair and the scalp in an amount corresponding to the dirt on the hair, foamed, and then the cleaning agent is washed away with water.

In addition, a method for washing hair or scalp which includes a step of applying a composition containing the above-mentioned components (A) to (E) and water to the hair or scalp is also included in the present invention. The definition and a preferably amount of each component, additional components and the like are as described above.

Furthermore, use of the above-mentioned components (A) to (E) for the production of a hair cleansing agent is also included in the present invention. The definition and a preferably amount of each component, additional components and the like are as described above.

In addition, use of the above-mentioned components (A) to (E) for washing hair or scalp is also included in the present invention. The definition and a preferably amount of each component, additional components and the like are as described above.

Other features of the invention will become apparent in the course of the following descriptions of exemplary embodiments which are given for illustration of the invention and are not intended to be limiting thereof.

EXAMPLES

1. Home Use Test
Preparation of Cleansing Agent

Respective components in the amounts shown in Table 1 were mixed, and the mixture was heated to 35 to 85° C. to uniformly dissolve each component. After cooling, 20% aqueous citric acid solution was added to adjust the pH to 5.46 to give liquid cleansing agents.

TABLE 1

| | component | Example 1 | Comp. Ex. 1 | Comp. Ex. 2 |
|---|---|---|---|---|
| | purified water | to 100 | to 100 | to 100 |
| C | polyquaternium-10 | 0.15 | 0.15 | 0.15 |
| A | Na cocoyl isethionate | | 2.50 | 2.50 |
| B | Na cocoyl glutamate (30%) | 8.50 | | |
| D | Na glutamate | 0.38 | | |
| A | Na (C14-16) olefin sulfonate (40%) | 25.00 | 25.00 | 25.00 |

TABLE 1-continued

| | component | Example 1 | Comp. Ex. 1 | Comp. Ex. 2 |
|---|---|---|---|---|
| | cocamide MIPA | 1.50 | 1.50 | 1.50 |
| | glyceryl stearate | 0.75 | 0.75 | 0.75 |
| | dioleic acid PEG-120 methylglucose | 0.50 | 0.50 | 0.50 |
| | cocamide propylhydroxy sultaine (50%) | 6.50 | 6.50 | 6.50 |
| | flavor | 0.30 | 0.30 | 0.30 |
| | methylchloroisothiazolinone methylisothiazolinone | 0.10 | 0.10 | 0.10 |
| D | amino acid mixture (50%) | 1.00 | | 1.00 |
| | 20% aqueous citric acid solution | to pH 5.46 | to pH 5.46 | to pH 5.46 |
| E | sodium chloride | 0.18 | 0.18 | 0.18 |

Numerical values are in wt %.

The home use test was conducted by a total of 10 people, 4 Japanese evaluators and 6 American evaluators. The evaluators used formulation samples for 2 days and evaluated them for the following items on the 2nd day.

(1) speed of lathering during hair washing, large lather amount, good finger passage through hair during foaming (2) smoothness of hair surface and good finger passage through hair during rinsing (3) smoothness of hair surface and good finger passage through hair as evaluation of wet hair after rinsing (4) smoothness of hair surface, moist feeling, and glossiness of hair after complete drying For evaluation, absolute evaluation was performed with 1 point as the lowest point and 5 points as the highest point, and the arithmetic mean is shown in Table 2.

TABLE 2

| | | Example 1 | Comp. Ex. 1 | Comp. Ex. 2 |
|---|---|---|---|---|
| during hair washing | speed of foaming | 3.7 | 3.9 | 3.4 |
| | large lather amount | 4.3 | 4.3 | 3.0 |
| | good finger passage through hair during foaming | 3.8 | 3.5 | 2.4 |
| during rinsing | smoothness of hair surface | 3.5 | 2.8 | 2.8 |
| | good finger passage through hair | 3.1 | 2.6 | 2.3 |
| evaluation of wet hair after rinsing | smoothness of hair surface | 3.0 | 2.8 | 2.8 |
| | good finger passage through hair | 3.0 | 2.8 | 2.8 |
| after complete drying | smoothness of hair surface | 3.5 | 2.8 | 3.1 |
| | moist feeling | 3.3 | 2.6 | 2.8 |
| | glossiness of hair | 3.8 | 2.8 | 2.9 |
| | total evaluation | 3.3 | 2.9 | 2.3 |

As compared with Comparative Examples 1 and 2, Example 1 showed high scores in almost all items, demonstrating the superiority of Example 1.

The detail of the components used is as follows.

polyquaternium-10: Ucare Polymer JR-400 (Nexeo/Dow) (nitrogen content 1.5-2.2 wt %)

Na cocoyl isethionate: Galsoft SCI-80 (Galaxy)

Na cocoyl glutamate (30%): Amisoft ECS-22W (Ajinomoto)

Na (C14-16) olefin sulfonate (40%): Bioterge AS-40K (Stepan) cocamide MIPA: Ninol M10 (Stepan)

dioleic acid PEG-120 methylglucose: Glucamate DOE-120 (Lubrizol)

cocamide propylhydroxysultaine (50%): Chembetaine CAS (Lubrizol)

flavor: Orange Coriander V11715 (Continental Aromatics) methylchloroisothiazolinone, methylisothiazolinone: Kathon CG (Dow Chemical)

amino acid mixture (50%): PRODEW500 (Ajinomoto) (containing 19.27% of PCA and 5.20% of aspartic acid)

2. Hair Bundle Evaluation

Preparation of Cleansing Agent

The formulations shown in Table 3 were prepared according to conventional methods and diluted 7-fold with tap water. The 7-fold dilution is used as a guideline in diluting hair shampoo when actually washing hair.

Test Method

Hair bundle evaluation was performed using Asian human hair (no history of chemical treatment) obtained from Beaulax. Hair bundles were soaked in a 7-fold diluted aqueous solution overnight, taken out, and evaluated for the following items.

(1) lather amount (2) good combability during cleansing (3) absence of friction on hair surface during rinsing (4) good combability during rinsing (5) softness of hair (6) good finger passage through hair after drying (7) glossiness after drying (8) softness of hair after drying (9) smoothness of hair after drying One professional panelist made the evaluation for each item based on an absolute evaluation of 1 to 5 points, and the arithmetic mean was calculated.

An arithmetic mean of not less than 3.5 points was marked with A, not less than 3.0 points and less than 3.5 points was marked with B, not less than 2.0 points and less than 3.0 points was marked with C, and less than 2 points was marked with D.

TABLE 3-1

| | | Example | | | | | | | | | | | |
|---|---|---|---|---|---|---|---|---|---|---|---|---|---|
| | component | 2 | 3 | 4 | 5 | 6 | 7 | 8 | 9 | 10 | 11 | 12 | 13 |
| C | polyquaternium-10 (2%) *1 | 7.5 | 7.5 | 7.5 | 7.5 | | 7.5 | 7.5 | 7.5 | 7.5 | 7.5 | 7.5 | 7.5 |
| C | polyquaternium-10 (2%) *2 | | | | | 7.5 | | | | | | | |
| | purified water | to 100 | to 100 | to 100 | to 100 | to 100 | to 100 | to 100 | to 100 | to 100 | to 100 | to 100 | to 100 |
| B | Na cocoyl glutamate (25%) | 8.5 | 7.0 | 7.0 | 7.0 | 7.0 | 8.5 | 8.5 | 8.5 | 8.5 | 8.5 | 8.5 | 8.5 |
| | lauric acid | | | | 0.5 | | | | | | | | |

TABLE 3-1-continued

|   |   | Example |||||||||||| 
|---|---|---|---|---|---|---|---|---|---|---|---|---|
|   | component | 2 | 3 | 4 | 5 | 6 | 7 | 8 | 9 | 10 | 11 | 12 | 13 |
|   | myristic acid |   |   |   |   |   |   |   |   |   |   |   |   |
| D | sodium glutamate | 0.38 | 0.50 | 0.50 | 0.50 | 0.50 | 0.38 | 0.38 | 0.38 | 0.38 | 0.38 | 0.38 |   |
| A | Na (C14-16) olefin sulfonate (37%) | 27.0 | 27.0 | 27.0 | 27.0 | 27.0 | 27.0 | 27.0 | 27.0 | 27.0 | 27.0 | 27.0 | 27.0 |
|   | lauramidohydroxysultaine (30%) | 10.8 | 10.8 | 10.8 | 10.8 | 10.8 | 10.8 | 10.8 | 10.8 | 10.8 | 10.8 | 10.8 | 10.8 |
| D | amino acid mixture (50%) | 1.0 | 1.0 | 1.0 |   | 1.0 | 1.0 |   |   |   |   |   | 1.0 |
|   | Na lactate (90%) |   |   |   |   |   |   | 0.13 |   |   |   |   |   |
| D | Na aspartate |   |   |   |   |   |   |   | 0.05 |   |   |   | 0.38 |
| E | arginine |   |   |   |   |   |   |   |   |   | 0.08 |   |   |
| F | glycine |   |   |   |   |   |   |   |   |   |   | 0.05 |   |
|   | alanine |   |   |   |   |   |   |   |   |   |   | 0.05 |   |
|   | 20% Na citrate | 1.8 | 1.8 | 1.8 | 1.8 | 1.8 | 1.8 | 1.8 | 1.8 | 1.8 | 1.8 | 1.8 | 1.8 |
| E | sodium chloride | 1.1 | 2.0 | 2.0 | 2.0 | 2.0 | 2.0 | 2.0 | 2.0 | 2.0 | 2.0 | 2.0 | 2.0 |
|   | total | 100 | 100 | 100 | 100 | 100 | 100 | 100 | 100 | 100 | 100 | 100 | 100 |
| evaluation item | lather amount | 3.0 | 3.0 | 3.0 | 3.0 | 3.0 | 3.0 | 3.0 | 3.0 | 3.0 | 3.0 | 3.0 | 3.0 |
|   | good combability during cleansing | 3.0 | 4.0 | 3.5 | 3.5 | 3.5 | 3.5 | 3.0 | 3.0 | 3.5 | 3.0 | 3.0 | 4.0 |
|   | absence of friction on hair surface during rinsing | 3.0 | 4.0 | 3.5 | 3.5 | 3.5 | 3.5 | 2.5 | 3.5 | 3.5 | 3.5 | 3.0 | 3.0 |
|   | good combability during rinsing | 3.0 | 3.5 | 2.0 | 2.5 | 3.5 | 3.5 | 2.5 | 3.5 | 3.5 | 3.5 | 3.0 | 4.0 |
|   | softness of hair | 3.0 | 3.5 | 2.0 | 2.5 | 3.5 | 3.5 | 2.5 | 3.5 | 3.5 | 3.5 | 3.0 | 4.0 |
|   | good finger passage through hair after drying | 3.0 | 4.5 | 3.5 | 4.0 | 4.0 | 4.5 | 4.0 | 4.0 | 4.0 | 3.0 | 3.0 | 3.0 |
|   | glossiness after drying | 3.0 | 4.0 | 3.0 | 4.0 | 4.0 | 4.0 | 4.0 | 4.0 | 4.0 | 3.5 | 3.5 | 3.5 |
|   | softness of hair after drying | 3.0 | 4.0 | 3.5 | 4.0 | 4.0 | 4.0 | 4.0 | 4.0 | 4.0 | 3.5 | 3.5 | 3.5 |
|   | smoothness of hair after drying | 3.0 | 3.5 | 3.5 | 3.5 | 3.5 | 3.5 | 4.0 | 4.0 | 4.0 | 3.5 | 3.5 | 3.0 |
|   | mean | 3.0 | 3.8 | 3.1 | 3.4 | 3.6 | 3.7 | 3.3 | 3.6 | 3.7 | 3.3 | 3.2 | 3.4 |
|   | evaluation | B | A | B | B | A | A | B | A | A | B | B | B |

Numerical values are in wt %.

TABLE 3-2

|   |   | Comparative Example |||||||||| 
|---|---|---|---|---|---|---|---|---|---|---|---|
|   | component | 3 | 4 | 5 | 6 | 7 | 8 | 9 | 10 | 11 | 12 |
| C | polyquaternium-10 (2%) *1 | 7.5 | 7.5 | 7.5 | 7.5 | 7.5 | 7.5 | 7.5 | 7.5 |   |   |
| C | polyquaternium-10 (2%) *2 |   |   |   |   |   |   |   |   |   |   |
|   | purified water | to 100 | to 100 | to 100 | to 100 | to 100 | to 100 | to 100 | to 100 | to 100 | to 100 |
| B | Na cocoyl glutamate (25%) | 8.5 | 7.0 | 7.0 | 8.5 | 8.5 |   |   | 8.5 | 8.5 | 8.5 |
|   | lauric acid |   | 0.5 |   | 0.38 |   |   |   |   |   |   |
|   | myristic acid |   |   | 0.5 |   | 0.38 |   |   |   |   |   |
| D | sodium glutamate |   |   |   |   |   | 0.38 |   |   |   | 0.38 |
| A | Na (C14-16) olefin sulfonate (37%) | 27.0 | 27.0 | 27.0 | 27.0 | 27.0 | 32.0 | 27.0 | 27.0 | 27.0 | 27.0 |
|   | lauramidohydroxysultaine (30%) | 10.8 | 10.8 | 10.8 | 10.8 | 10.8 | 10.8 | 10.8 | 10.8 | 10.8 | 10.8 |
| D | amino acid mixture (50%) | 1.0 | 1.0 | 1.0 | 1.0 | 1.0 | 1.0 | 1.0 |   | 1.0 | 1.0 |
|   | Na lactate (90%) |   |   |   |   |   |   |   |   |   |   |
| D | Na aspartate |   |   |   |   |   |   |   |   | 0.38 |   |
| F | arginine |   |   |   |   |   |   |   |   |   |   |
|   | glycine |   |   |   |   |   |   |   |   |   |   |
| F | alanine |   |   |   |   |   |   |   |   |   |   |
|   | 20% Na citrate | 1.8 | 1.8 | 1.8 | 1.8 | 1.8 | 1.8 | 1.8 | 1.8 | 1.8 | 1.8 |
| E | sodium chloride | 2.0 | 2.0 | 2.0 | 2.0 | 2.0 | 2.0 | 2.0 | 2.0 | 2.0 | 2.0 |
|   | total | 100 | 100 | 100 | 100 | 100 | 100 | 100 | 100 | 100 | 100 |
| evaluation item | lather amount | 3.0 | 3.0 | 2.0 | 3.0 | 3.0 | 3.0 | 3.0 | 3.0 | 3.0 | 3.0 |
|   | good combability during cleansing | 3.0 | 2.0 | 1.0 | 1.5 | 1.0 | 3.0 | 3.0 | 2.0 | 2.0 | 2.0 |

TABLE 3-2-continued

| | Comparative Example | | | | | | | | | |
|---|---|---|---|---|---|---|---|---|---|---|
| component | 3 | 4 | 5 | 6 | 7 | 8 | 9 | 10 | 11 | 12 |
| absence of friction on hair surface during rinsing | 2.5 | 2.0 | 1.0 | 1.5 | 1.0 | 3.0 | 2.5 | 2.0 | 1.5 | 2.0 |
| good combability during rinsing | 3.0 | 2.0 | 1.0 | 1.5 | 0.5 | 3.0 | 2.0 | 2.0 | 2.0 | 3.0 |
| softness of hair | 3.0 | 2.0 | 1.0 | 1.5 | 1.0 | 3.0 | 3.0 | 2.0 | 2.0 | 3.0 |
| good finger passage through hair after drying | 3.0 | 3.0 | 2.0 | 2.5 | 2.0 | 3.0 | 3.0 | 3.0 | 3.0 | 3.0 |
| glossiness after drying | 3.0 | 3.0 | 2.5 | 3.0 | 3.0 | 3.0 | 3.0 | 2.5 | 3.0 | 3.0 |
| softness of hair after drying | 3.0 | 3.0 | 3.0 | 2.5 | 2.5 | 2.5 | 3.0 | 3.0 | 3.0 | 3.5 |
| smoothness of hair after drying | 2.5 | 2.5 | 2.5 | 2.5 | 2.0 | 2.5 | 3.5 | 3.0 | 2.5 | 3.5 |
| mean | 2.9 | 2.5 | 1.8 | 2.2 | 1.8 | 2.9 | 2.9 | 2.5 | 2.4 | 2.9 |
| evaluation | C | C | D | C | D | C | C | C | C | C |

Numerical values are in wt %.

The results are shown in Table 3. As compared with Comparative Examples, Examples showed superior results in the texture during washing, during rinsing, and after drying of hair.

The detail of the components used is as follows.
polyquaternium-10(2%)*1: JR-400 (Dow) (nitrogen content 1.5-2.2 wt %)
polyquaternium-10(2%)*2: LEOGARD GP (Lion Specialty Chemicals) (nitrogen content 1.6-2 wt %)
Na cocoyl glutamate (25%): CS-22 (Ajinomoto)
lauric acid: NAA122 (NOF CORPORATION)
myristic acid: NAA142 (NOF CORPORATION)
sodium glutamate: (Ajinomoto)
Na (C14-16) olefin sulfonate (37%): LIPOLAN LB440 (Lion)
lauramidohydroxysultaine (30%): Softazoline LSB (Kawaken Fine Chemicals)
amino acid mixture (50%): PRODEW500 (Ajinomoto) (containing 19.27% of PCA and 5.20% of aspartic acid)
Na lactate (90%): Na lactate (Wako Pure Chemical Industries, Ltd.)
Na aspartate: Na aspartate (Ajinomoto)
arginine: arginine (Ajinomoto)
glycine: glycine (Ajinomoto)
alanine: alanine (Ajinomoto)
Na citrate: citric acid crystal (FUSO CHEMICAL CO., LTD.)
sodium chloride: sodium chloride (Tokyo Chemical Industry Co., Ltd.)

INDUSTRIAL APPLICABILITY

The present invention can provide a hair cleansing agent superior in foaming and lather amount, and achieving good sense of use.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A hair cleansing agent, comprising the following components: (A) to (F) and water:
    (A) not less than 3 wt % and not more than 12 wt %, based on the total weight of said agent, of one or more members selected from the group consisting of an acyl isethionate and an α-olefin sulfonate,
    (B) not less than 0.5 wt % and not more than 10 wt %, based on the total weight of said agent, of cocoylglutamic acid or a salt thereof,
    (C) not less than 0.005 wt % and not more than 0.8 wt %, based on the total weight of said agent, of at least one cationic polymer,
    (D) not less than 0.3 wt % and not more than 3 wt %, based on the total weight of said agent, of two or more members selected from the group consisting of glutamic acid, aspartic acid, pyrrolidonecarboxylic acid, and salts thereof,
    (E) more than 1.1 wt % and not more than 5 wt %, based on the total weight of said agent, of at least one inorganic salt selected from sodium chloride, potassium chloride and magnesium chloride, and
    (F) not less than 0.01 wt % and not more than 2 wt %, based on the total weight of said agent, of at least one basic or neutral amino acid,
    wherein said agent has a pH of less than 7.

2. The hair cleansing agent according to claim 1, wherein said component (C) at least one cationic polymer has a nitrogen content of not less than 1.5 wt % and not more than 2.2 wt %.

3. The hair cleansing agent according to claim 1, wherein said (E) at least one inorganic salt is sodium chloride.

4. The hair cleansing agent according to claim 1, wherein said agent is in a liquid form.

5. The hair cleansing agent according to claim 1, wherein component (F) is a neutral amino acid.

6. The hair cleansing agent according to claim 5, wherein the neutral amino acid is glycine and/or alanine.

7. The hair cleansing agent according to claim 4, wherein said agent has a pH of 4.8 to 6.8.

8. The hair cleansing agent according to claim 1, wherein the content of component (D) is not less than 0.3 wt % and not more than 2 wt %, based on the total weight of said agent.

9. The hair cleansing agent according to claim 1, wherein the content of (B) is not less than 0.5 wt % and not more than 3 wt %, based on the total weight of said agent.

* * * * *